United States Patent
Miskie

(10) Patent No.: US 7,815,619 B2
(45) Date of Patent: Oct. 19, 2010

(54) RECEPTACLE FOR A MALE INCONTINENCE DEVICE

(75) Inventor: Mark Miskie, Charlotte, NC (US)

(73) Assignee: Arcus Medical, LLC, Charlotte, NC (US)

( * ) Notice: Subject to any disclaimer, the term of this patent is extended or adjusted under 35 U.S.C. 154(b) by 0 days.

(21) Appl. No.: 11/584,894

(22) Filed: Oct. 23, 2006

(65) Prior Publication Data

US 2007/0038193 A1 Feb. 15, 2007

Related U.S. Application Data

(63) Continuation of application No. 10/983,828, filed on Nov. 8, 2004, now Pat. No. 7,125,399, which is a continuation of application No. PCT/US02/34541, filed on Oct. 28, 2002.

(51) Int. Cl.
*A61F 5/44* (2006.01)

(52) U.S. Cl. .................. 604/349; 604/347; 604/350

(58) Field of Classification Search .......... 604/346, 604/347, 349, 350
See application file for complete search history.

(56) References Cited

U.S. PATENT DOCUMENTS

| | | | |
|---|---|---|---|
| 3,604,424 A | 9/1971 | Windom | |
| 3,626,941 A | 12/1971 | Webb | |
| 3,651,810 A | 3/1972 | Ormerod | |
| 4,020,843 A | 5/1977 | Kanall | |
| 4,022,213 A | 5/1977 | Stein | |
| 4,387,726 A | 6/1983 | Denard | |
| 5,478,334 A | 12/1995 | Bernstein | |
| 6,565,545 B1 * | 5/2003 | Frenche | 604/349 |
| 7,104,975 B2 * | 9/2006 | Vantroostenberghe | 604/350 |

* cited by examiner

Primary Examiner—Tatyana Zalukaeva
Assistant Examiner—Lynne Anderson
(74) Attorney, Agent, or Firm—Schwartz Law Firm, P.C.

(57) ABSTRACT

A multi-piece fluid transfer receptacle is used in a male incontinence device. The receptacle includes an outer shell having a first open end adapted for receiving the penis of a user and a second end defining a fluid discharge port. The second end extends beyond the first end a distance sufficient to cover a head of the penis, whereby urine is transferred forwardly from the penis and outwardly from the receptacle through the discharge port. A detachable fluid-management insert is received within the first open end and includes an elongated tongue spaced apart from an interior surface of the outer shell. The tongue forms a backflow barrier between the penis and the outer shell to shield the penis from urine flowing backward towards the user and away from the discharge port.

13 Claims, 9 Drawing Sheets

RECEPTACLE FOR A MALE INCONTINENCE DEVICE

TECHNICAL FIELD AND BACKGROUND OF THE INVENTION

This invention relates generally to male incontinence, and more specifically to a receptacle adapted for use in a male incontinence device. The invention fits securely and comfortably on the user without adhesives, tape, glue, or other constricting elements which may irritate and injure the skin. The invention is relatively inconspicuous under clothing, and provides a freedom of movement often sacrificed with commercially available male incontinence devices and catheters. Users can wear the present invention with confidence and without a feeling of self-consciousness.

Incontinence is a growing problem, particularly in those adults ages 65 and older. Approximately four million males in the United States suffer from varying degrees of incontinence. Common causes for this condition include an enlarged prostate, prostate cancer, pelvic trauma, spinal cord injury, and medication side-effects. Over $16 billion is spent annually on incontinence related care.

The present invention addresses the limitations of certain prior art devices and catheters used for managing male incontinence. Specifically, the invention provides a "comfort wear" external device that is both effective and easy to use, and which resides generally unnoticed inside the clothing of the wearer without creating a feeling of self-consciousness. The invention is also applicable for monitoring the amount of urine expelled by patients in bladder training following prostate surgery, or radiation treatments. While not a cure for male urinary incontinence, the invention is intended to allow for a better quality of life with less skin irritation and fewer problems as compared to present, commercially available and accepted incontinent devices.

SUMMARY OF THE INVENTION

Therefore, it is an object of the invention to provide a receptacle for a male incontinence device which is effective and comfortable to wear.

It is another object of the invention to provide a receptacle for a male incontinence device which is non-irritating to the skin, and which does not use adhesives, tape, glue or other constricting elements attached directly to the penis.

It is another object of the invention to provide a receptacle for a male incontinence device which is easy to maintain and clean.

It is another object of the invention to provide a receptacle for a male incontinence device which has an ergonomic design for increased comfort.

It is another object of the invention to provide a receptacle for a male incontinence device which is easily concealed under clothing.

It is another object of the invention to provide a receptacle for a male incontinence device which is designed such that one size fits a majority of users.

It is another object of the invention to provide a receptacle for a male incontinence device which is relatively easy to put on and remove.

It is another object of the invention to provide a receptacle for a male incontinence device which is especially designed for active adults.

It is another object of the invention to provide a receptacle for a male incontinence device which can be readily disassembled for cleaning and parts replacement, if necessary.

It is another object of the invention to provide a receptacle for a male incontinence device which reduces the incidence of urinary tract infections.

It is another object of the invention to provide a receptacle for a male incontinence device which allows air circulation between the receptacle and penis of the wearer.

These and other objects of the present invention are achieved in the preferred embodiments disclosed below by providing a multi-piece fluid transfer receptacle for a male incontinence device. The receptacle includes an outer shell having a first open end adapted for receiving the penis of a user and a second end defining a fluid discharge port. The second end extends beyond the first end a distance sufficient to cover a head of the penis, whereby urine is transferred forwardly from the penis and outwardly from the receptacle through the discharge port. A detachable fluid-management insert is received within the first open end and includes an elongated tongue spaced apart from an interior surface of the outer shell. The tongue forms a backflow barrier between the penis and the outer shell to shield the penis from urine flowing backward towards the user and away from the discharge port.

Preferably, the outer shell of the receptacle covers the full length of the penis.

The term "multi-piece" refers to pieces which are separately formed and subsequently assembled, or which are integrally-formed together as a single unit.

The fluid transfer insert is preferably detachable as a separate piece. In an alternative preferred embodiment, the fluid transfer insert is integrally-formed together with the outer shell.

According to another preferred embodiment of the invention, the tongue of the fluid-management insert includes drain holes for allowing passage of urine therethrough.

According to another preferred embodiment of the invention, a plurality of spacers are located between the tongue and the interior surface of the outer shell.

According to another preferred embodiment of the invention, the fluid-management insert further includes an attachment ring integrally-formed with the tongue and adapted to fit over an annular edge of the first open end of the outer shell.

According to another preferred embodiment of the invention, the attachment ring includes an outwardly-turned annular lip adapted to snap-fit over a complementary annular shoulder formed with the first open end of the outer shell.

According to another preferred embodiment of the invention, the tongue of the fluid-management insert has a generally cylindrical base integrally-formed with the attachment ring and spaced-apart from the interior surface of the outer shell to capture urine flowing backward towards the user and away from the discharge port.

The term "generally cylindrical" is used broadly herein to mean cylindrical, or having an oval or elliptical shaped cross-section.

According to another preferred embodiment of the invention, the outer shell is formed of a shape-retaining material having an arcuate, ergonomic design.

According to another preferred embodiment of the invention, the fluid-management insert is formed of an antimicrobial plastic.

According to another preferred embodiment of the invention, the second end of the outer shell has a reduced-diameter neck.

According to another preferred embodiment of the invention, the neck includes an external screw thread adapted for mating with a complementary, internally-threaded cap of a urine collection bag. Alternatively, a separate internally-threaded cap may be used in combination with either an elongated drain tube or a disposable collection bag fixed to the receptacle using an adhesive tape.

According to another preferred embodiment of the invention, the neck is offset from a notional centerline to reduce puddling at the discharge port of the outer shell.

According to another preferred embodiment of the invention, a one-way valve is located at the discharge port of the outer shell for providing one-way flow of urine outwardly from the receptacle. The one-way valve may be located within the collection bag or embedded in the internally-threaded cap.

In yet another embodiment, the receptacle includes an outer shell having a first open end adapted for receiving the penis of a user and a second end defining a fluid discharge port. The second end extends beyond the first end a distance sufficient to cover a head of the penis, whereby urine is transferred forwardly from the penis and outwardly from the receptacle through the discharge port. A fluid-management insert is received within the first open end. The insert includes an elongated tongue spaced apart from an interior surface of the outer shell and defining a plurality of drain holes for allowing passage of urine therethrough. The tongue forms a backflow barrier between the penis and the outer shell to shield the penis from urine flowing backward towards the user and away from the discharge port.

In yet another embodiment, the invention is a male incontinence device including a multi-piece fluid transfer receptacle.

Preferably, the incontinence device further includes a collection bag secured to the second end of the outer shell and adapted for receiving and collecting urine flowing outwardly through the discharge port.

BRIEF DESCRIPTION OF THE DRAWINGS

Some of the objects of the invention have been set forth above. Other objects and advantages of the invention will appear as the description proceeds when taken in conjunction with the following drawings, in which.

DESCRIPTION OF THE PREFERRED EMBODIMENT AND BEST MODE

Figure 1:
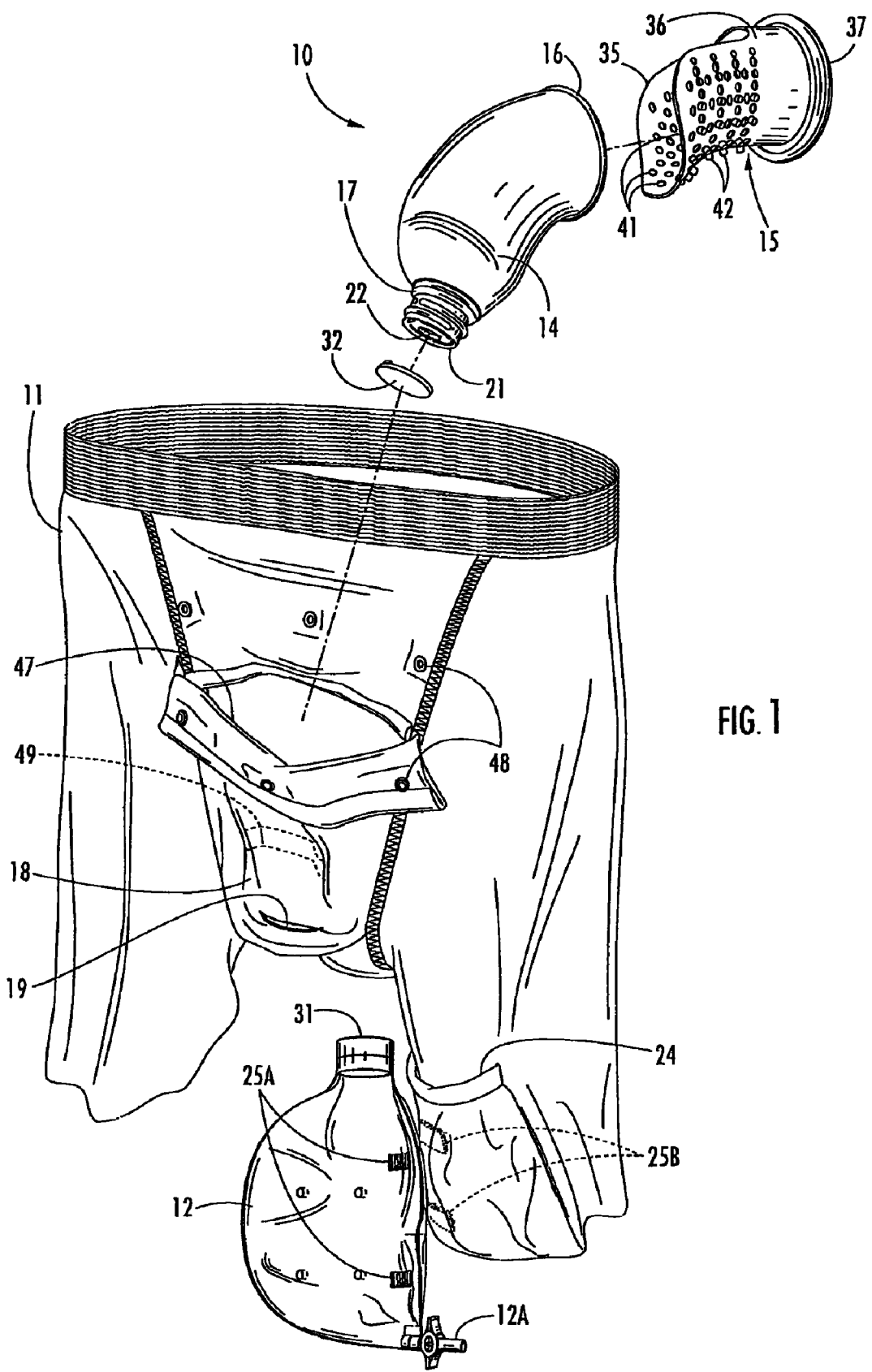
FIG. 1 is a perspective view of an incontinence management system with components of the system exploded away.

Referring now specifically to the drawings, a multi-piece fluid transfer receptacle for a male incontinence device according to the present invention is illustrated in FIG. 1, and shown generally at reference numeral 10. The multi-piece receptacle 10 is especially adapted for use in an incontinence management system including a supporting undergarment 11 and collection bag 12. The receptacle 10 comprises an ergonomically-designed, shape-retaining outer shell 14 and a detachable fluid-management insert 15. The outer shell 14 and insert 15 are preferably formed of a lightweight, flexible, soft, resilient, antimicrobial plastic.

Figure 2:
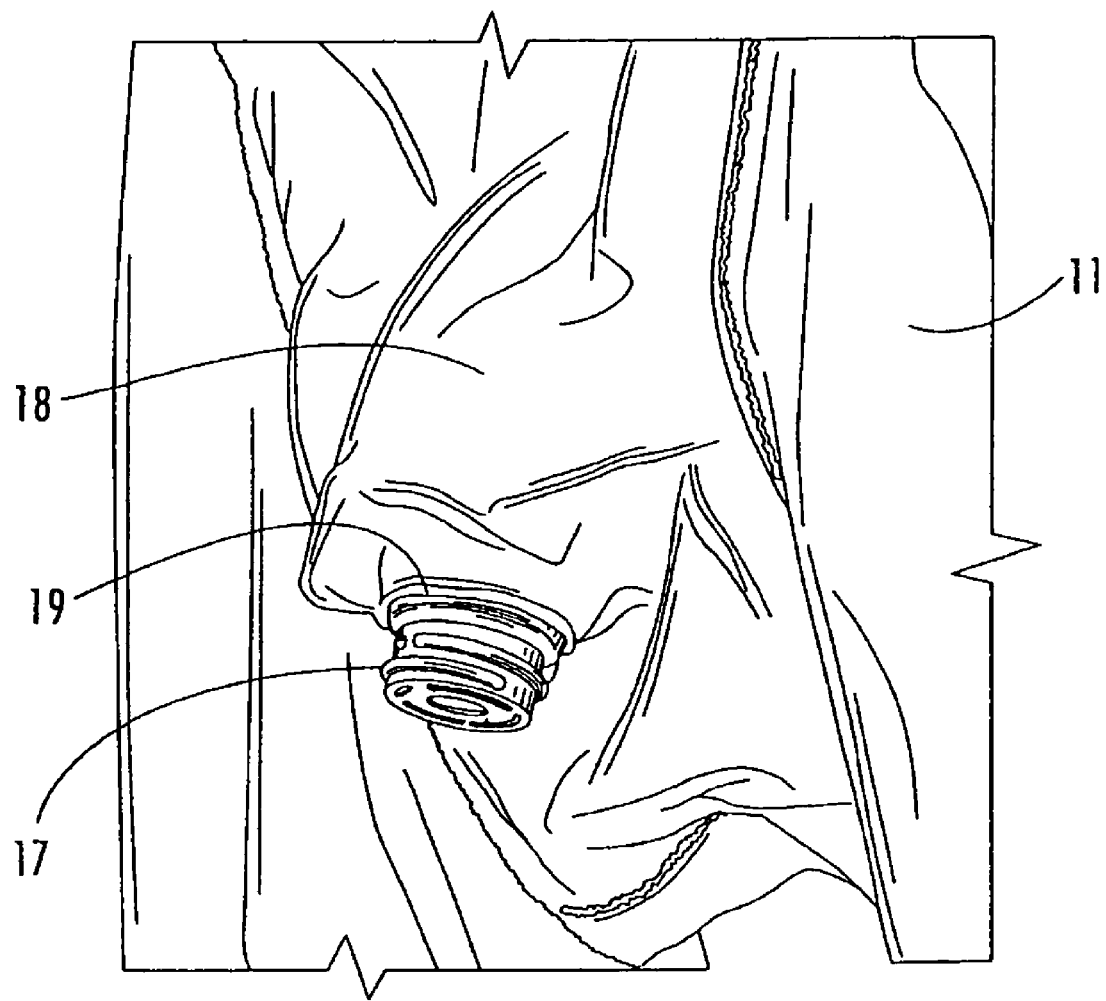
FIG. 2 is a fragmentary view of the undergarment showing the neck of the fluid transfer receptacle exposed for attachment to the urine collection bag.
Figure 3:
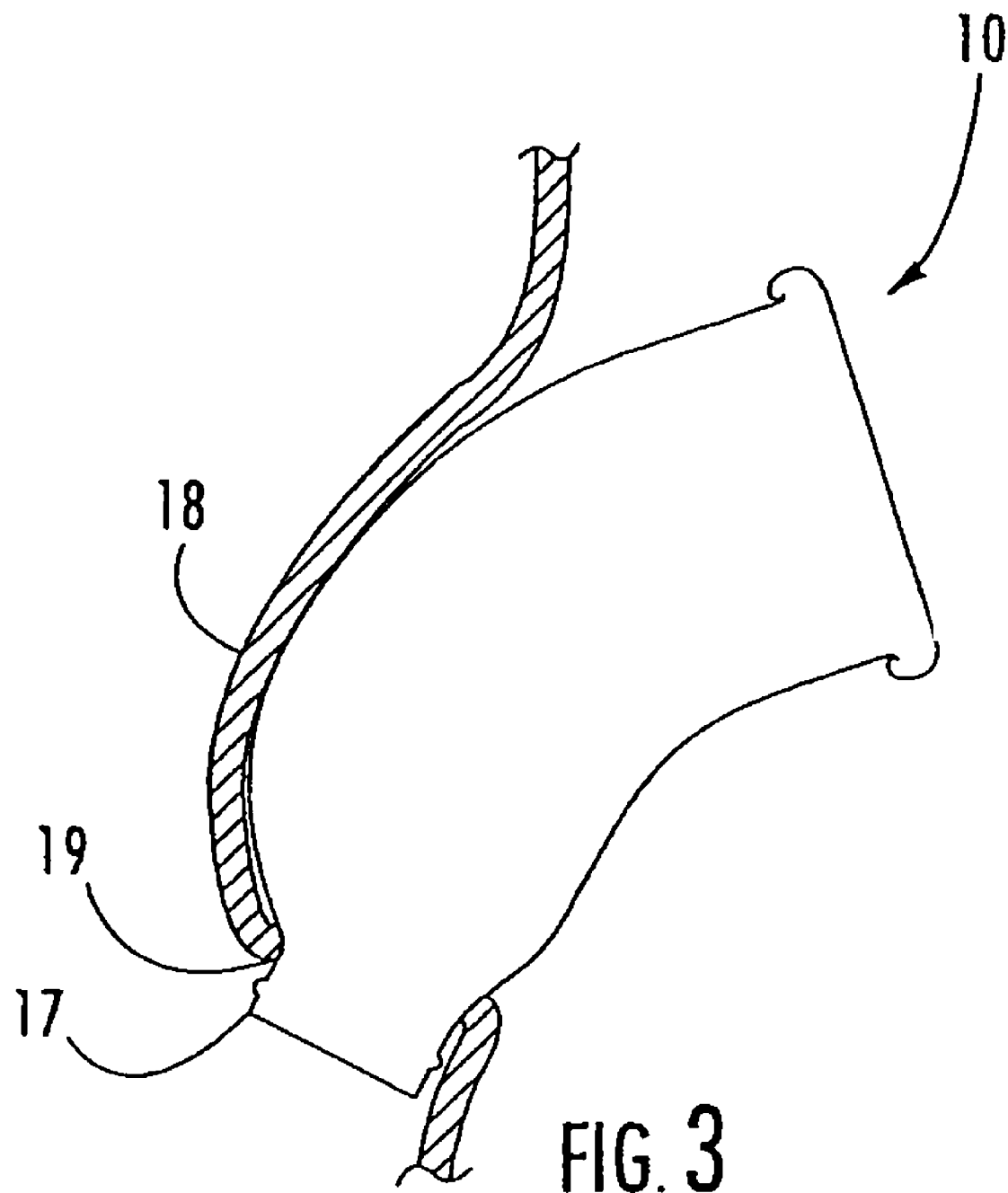
FIG. 3 is a fragmentary sectional view of the undergarment illustrating the location of the receptacle.

The outer shell 14 has a relatively large diameter open end 16 adapted for receiving the penis of a user, and an opposite end defining an elongated reduced-diameter neck 17. The neck 17 is designed to penetrate a crotch panel 18 of the undergarment 11 through a receptacle slit 19, shown in FIGS. 1, 2, and 3. An end wall 21 of the neck 17 defines a fluid discharge port 22 through which urine passes outwardly from the receptacle 10 and into the collection bag 12. The collection bag 12 attaches to the neck 17, as described below, and fits loosely within a leg pocket 24 formed with the undergarment 11. The collection bag 12 is releasably retained inside the pocket using complementary patches of hook and loop fasteners 25A and 25B. When the collection bag 12 is full, urine is drained through an outlet valve 12A.

Figure 4:
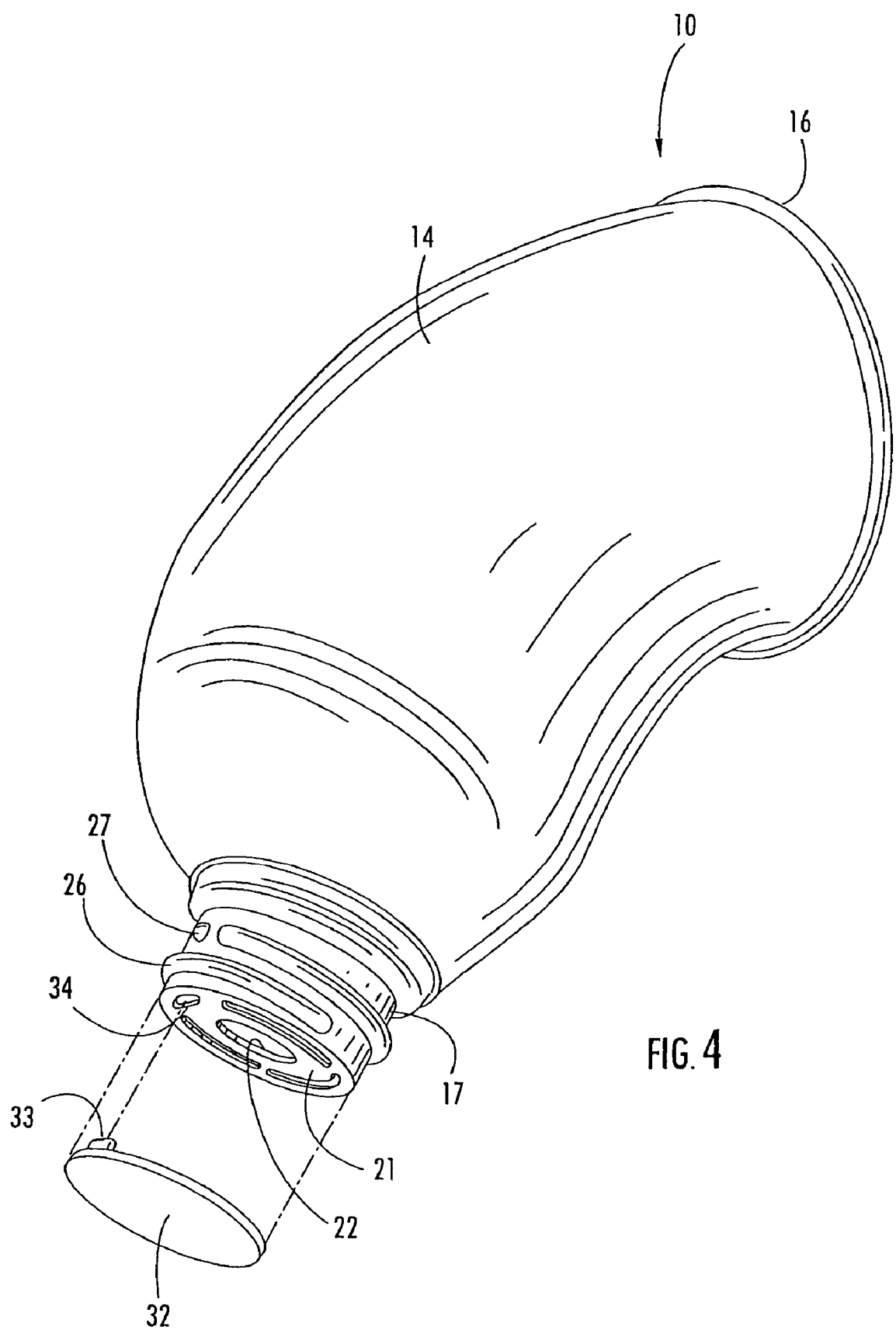
FIG. 4 is a perspective view of the receptacle showing the one-way flap valve exploded away.
Figure 5:
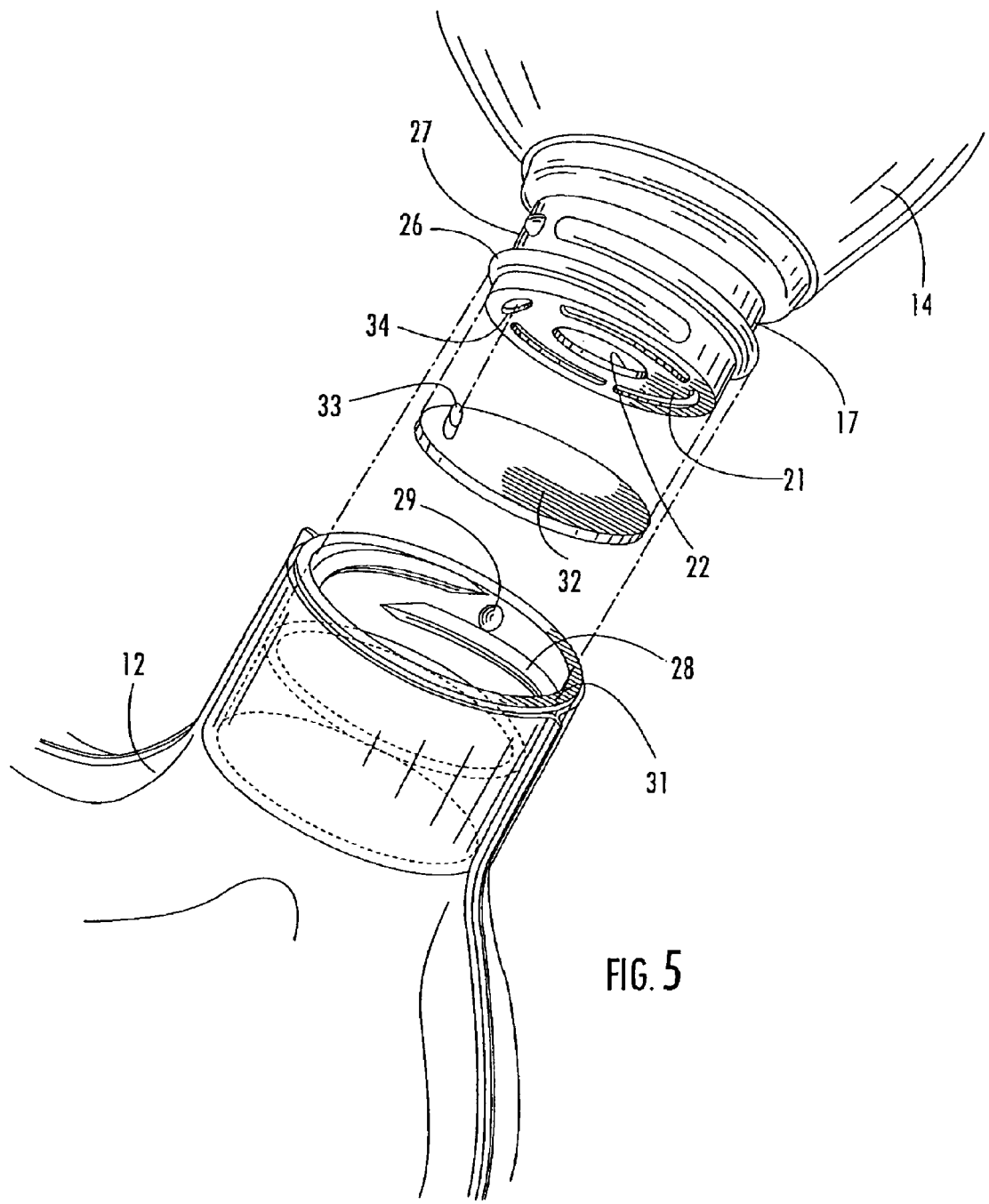
FIG. 5 is an enlarged, fragmentary perspective view of the receptacle and collection bag exploded away to illustrate the sealed, threaded connection of these components.

As shown in FIGS. 4 and 5, the neck 17 of the outer shell 14 has an external screw thread 26 and locking detent 27. The screw thread 26 and detent 27 mate with a complementary internal thread 28 and dimple 29 (FIG. 5) formed with a cap 31 of the collection bag 12. Mating alignment of the detent 27 and dimple 29 indicates a properly sealed, interlocking connection between the receptacle 10 and bag 12.

A disk-shaped, one-way flap valve 32 is located between the discharge port 22 of the outer shell 14 and the collection bag 12 to control the flow of urine from the receptacle 10 to the bag 12. The flap valve 32 sits adjacent the neck 17, and includes a resilient attachment post 33 which fits within a small opening 34 formed in the end wall 21 of the outer shell 14 adjacent the discharge port 22. The post 33 creates a hinge which urges the valve 32 into a normally closed condition seated against the end wall 21 and covering the discharge port 22 to prevent any backflow of urine from the collection bag 12 into the receptacle 10. With the occurrence of slight fluid pressure inside the receptacle 10, the flap valve 32 swings outwardly to an open condition allowing urine to flow outwardly from the receptacle 10 and into the collection bag 12. Preferably, the discharge port 22 is a series of strategically formed and spaced-apart openings designed to promote effective one-way operation and sealing of the flap valve 32.

Figure 6:
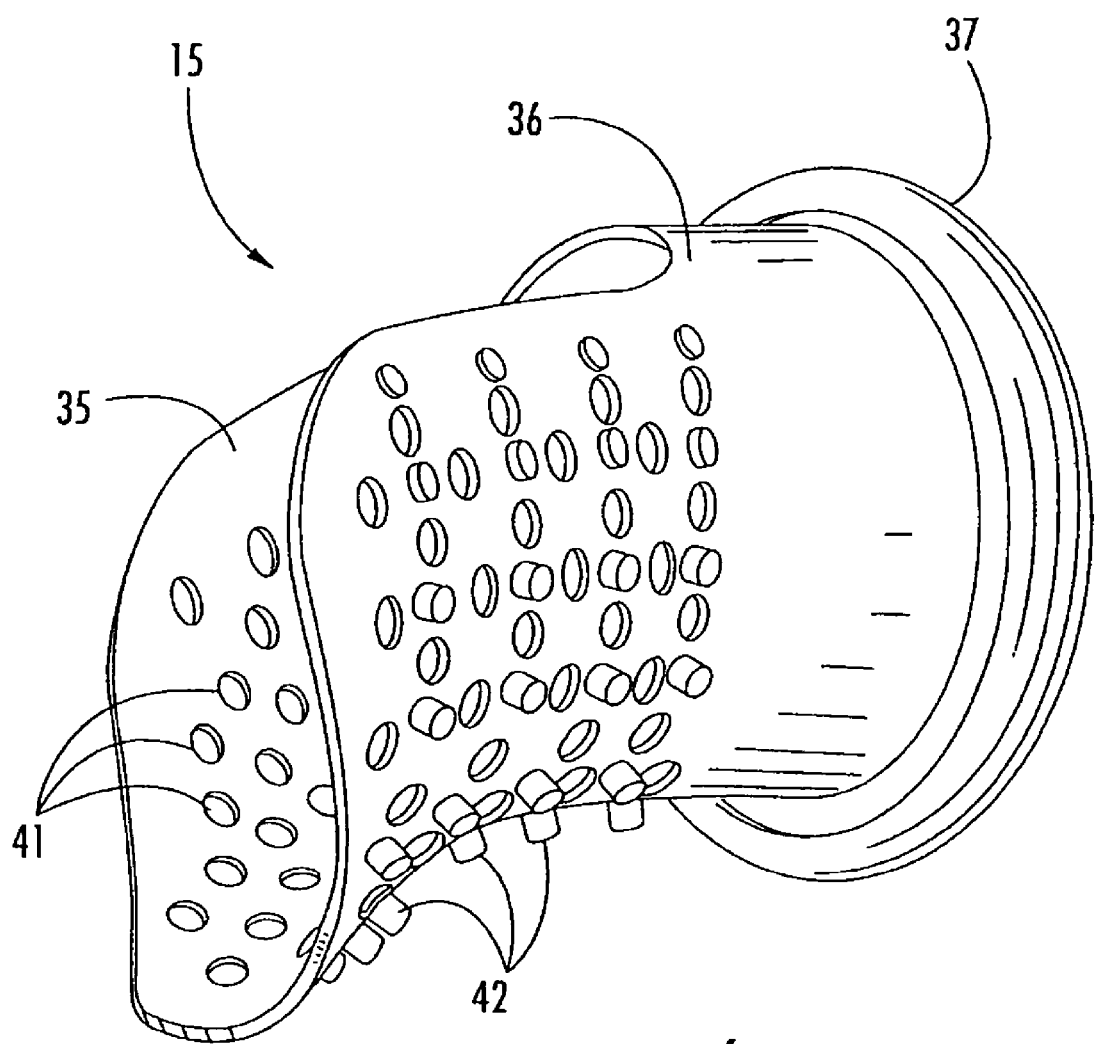
FIG. 6 is a perspective view of the fluid-management insert.
Figure 7:
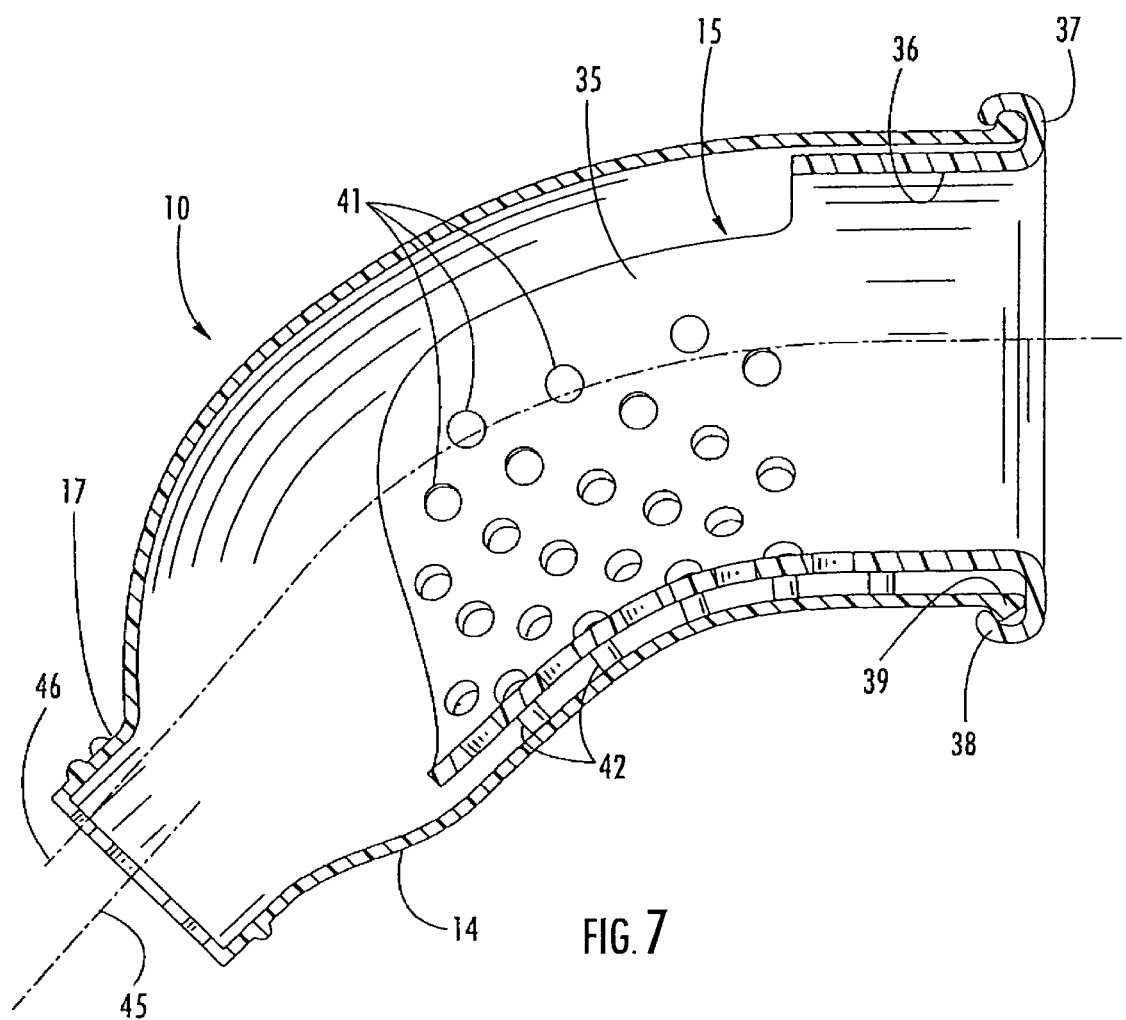
FIG. 7 is a cross-sectional view of the receptacle showing the outer shell and insert in an assembled condition.

Referring to FIGS. 1, 6, and 7, the fluid-management insert 15 carries the penis of the user inside the receptacle 10 and is detachably received within the open end 16 of the outer shell 14. The fluid-management insert 15 includes a perforated tongue 35, a generally cylindrical base 36, and a rounded attachment ring 37. The attachment ring 37 has an outwardly-turned annular lip 38, best shown in FIG. 7, which snap fits over a complementary annular shoulder 39 formed with the open end 16 of the outer shell 14. The convenient snap-attachment of the outer shell 14 and insert 15 allows ready assembly and disassembly of the receptacle 10 for cleaning and/or parts replacement. The cylindrical base 36 is integrally-formed with the attachment ring 37 and slightly spaced-apart from the interior surface of the outer shell 14. The perforated tongue 35 is integrally-formed with the cylindrical base 36, and extends inwardly adjacent the contours of the outer shell 14. The perforations promote ventilation inside the receptacle 10 and form drain holes 41 in the tongue 35 to permit the passage of urine away from the penis. Preferably, the combined length of the tongue 35 and base 36 is greater than 50% of the length of the outer shell 14. Post spacers 42 are formed with an underside of the tongue 35 and engage the interior surface of the outer shell 14 to create a backflow passage between the tongue 35 and the outer shell 14.

Figure 8:
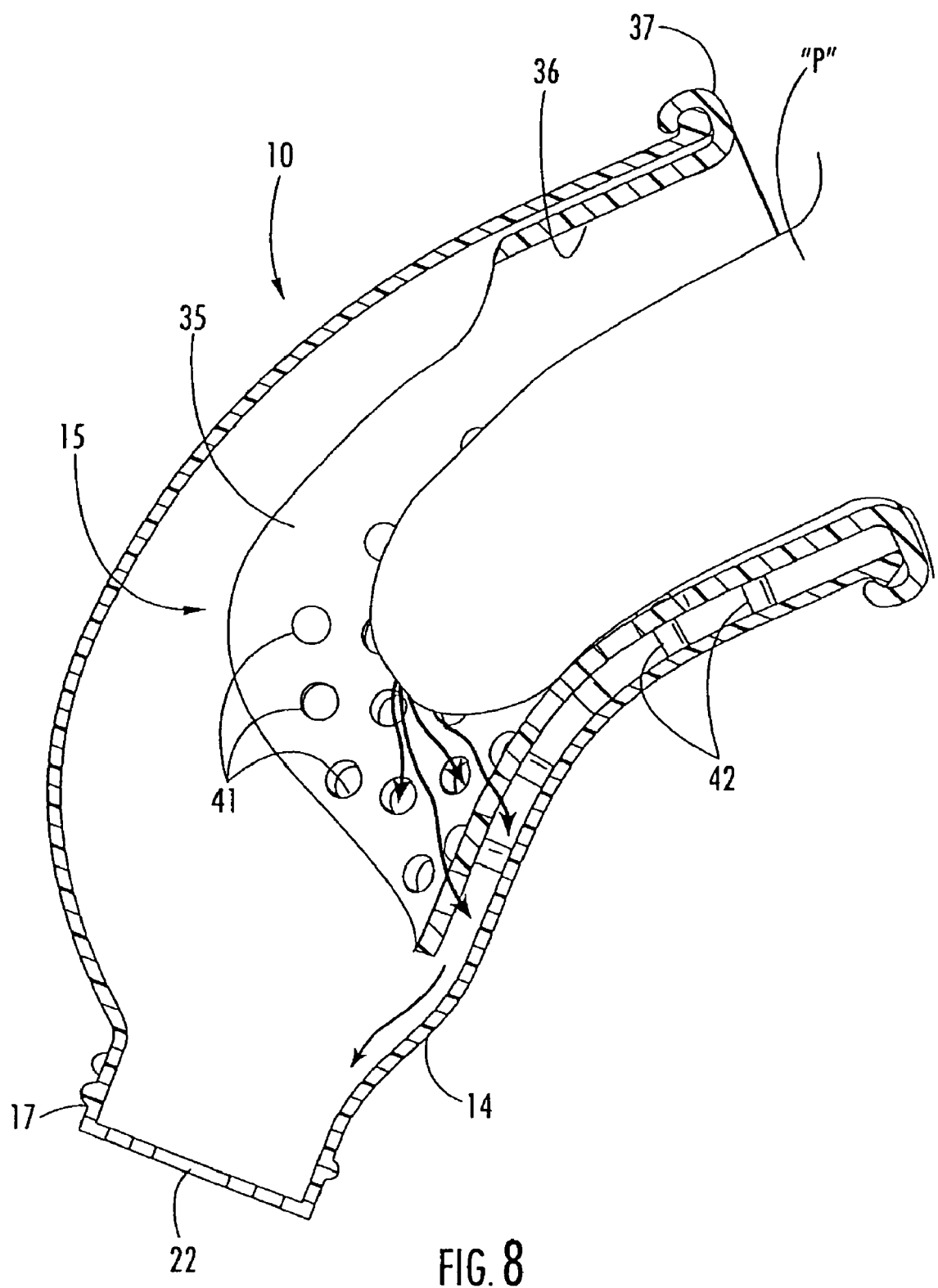
FIG. 8 is a cross-sectional view of the receptacle showing the passage of urine through drain holes in the tongue and downwardly towards the discharge port of the outer shell.
Figure 9:
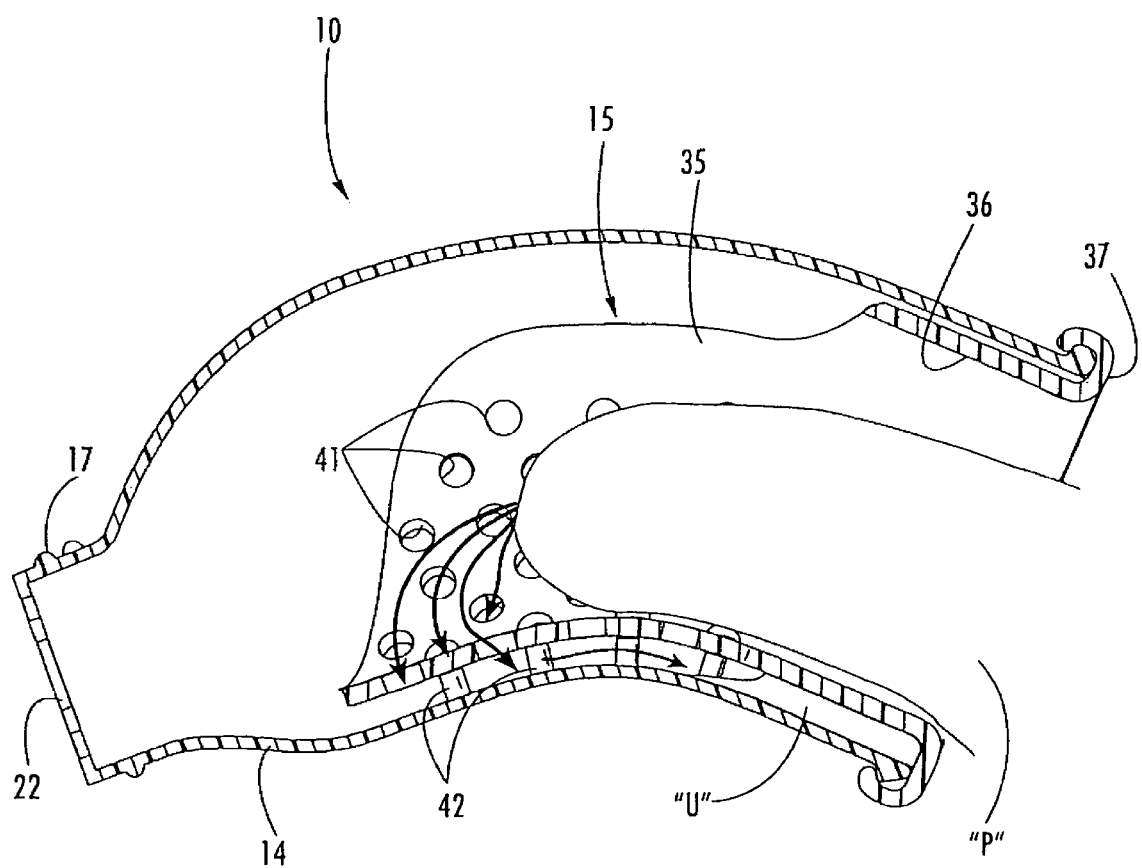
FIG. 9 is a cross-sectional view of the receptacle showing the passage of urine through drain holes and flowing backwardly towards the user.

When in a normal standing position, the receptacle 10 is generally oriented inside the undergarment as shown in FIG. 8. In this position, urine flows downwardly from the penis "P" through the drain holes 41 in the tongue 35, and outwardly through the discharge port 22 in the outer shell 14 of the receptacle 10 to the attached collection bag (not shown). Alternatively, for hospital patients or other individuals confined to a bed or wheelchair, an elongated drain tube may be fixed to the neck 17 of the outer shell 14. In order to prevent or limit puddling of urine inside the receptacle 10, the neck 17 of the outer shell 14 extends along an axis 45 offset from a notional center axis 46 of the receptacle 10, as shown in FIG. 7. When seated or in a supine position, the receptacle 10 is generally oriented in a more horizontal position. In this position, shown in FIG. 9, some amount of urine "U" may flow through the drain holes 41 in the tongue 35 and backwardly towards the user. The tongue 35 provides a backflow barrier between the penis "P" and outer shell 14. In this case, urine "U" is shielded from the penis "P" and captured between the solid-wall cylindrical base 36 and outer shell 14. The cylindrical base 36 extends 360 degrees around an inner margin of the open end 16 of the outer shell 14, and cooperates with the raised walls of the tongue 35, integrally-formed attachment ring 37, and multiple drain openings 41 to provide complete protection against any backflow leakage of urine from the receptacle 10.

For convenient access to the receptacle 10 and to enable normal urination outside of the receptacle 10, the undergarment 11 preferably includes a horizontal fly 47 which is opened and closed using snap fasteners 48 shown in FIG. 1. In addition, the receptacle 10 may be further retained inside the undergarment 11 by an inside elastic strap 49.

A multi-piece fluid transfer receptacle for a male incontinence device is described above. Various details of the invention may be changed without departing from its scope. Furthermore, the foregoing description of the preferred embodiment of the invention and best mode for practicing the invention are provided for the purpose of illustration only and not for the purpose of limitation—the invention being defined by the claims.

I claim:

1. A fluid transfer receptacle for a male incontinence device, said receptacle comprising:
    an outer shell having a first open end adapted for receiving the penis of a user and a second end defining a fluid discharge port, the second end extending beyond the first end a distance sufficient to cover a head of the penis, whereby urine is transferred forwardly from the penis and outwardly from said receptacle through said discharge port; and said outer shell having a longitudinal dimension extending along an arcuate notional axis from the first end to the second end thereof;
    an elongated longitudinally arcuate tongue spaced apart from said outer shell and extending along a longitudinally arcuate interior surface of said outer shell, and said tongue having contoured peripheral edges adapted to only partially surround a length of the penis during use; and
    at least one spacer located intermediate the contoured peripheral edges of said tongue, and between said tongue and the interior surface of said outer shell.

2. A fluid transfer receptacle according to claim 1, and comprising an attachment ring integrally-formed with said tongue and adapted to fit over an annular edge of the first open end of said outer shell.

3. A fluid transfer receptacle according to claim 2, wherein said attachment ring comprises an outwardly-turned annular lip adapted to snap-fit over a complementary annular shoulder formed with the first open end of said outer shell.

4. A fluid transfer receptacle according to claim 3, wherein said tongue comprises a generally cylindrical base integrally-formed with said attachment ring and spaced-apart from the interior surface of said outer shell to capture urine flowing backward towards the user and away from said discharge port.

5. A fluid transfer receptacle according to claim 1, wherein said outer shell is formed of a shape-retaining material having an arcuate, ergonomic design.

6. A fluid transfer receptacle according to claim 1, wherein said tongue is formed of an antimicrobial plastic.

7. A fluid transfer receptacle according to claim 1, wherein the second end of said outer shell comprises a reduced-diameter neck.

8. A fluid transfer receptacle according to claim 7, wherein said neck comprises an external screw thread adapted for mating with a complementary, internally-threaded cap of a urine collection bag.

9. A fluid transfer receptacle according to claim 7, wherein said neck is offset from a notional centerline to reduce puddling at the discharge port of said outer shell.

10. A fluid transfer receptacle according to claim 1, and comprising a one-way valve located at the discharge port of said outer shell for providing one-way flow of urine outwardly from said receptacle.

11. A male incontinence device including a fluid transfer receptacle, said receptacle comprising:
    an outer shell having a first open end adapted for receiving the penis of a user and a second end defining a fluid discharge port, the second end extending beyond the first end a distance sufficient to cover a head of the penis, whereby urine is transferred forwardly from the penis and outwardly from said receptacle through said discharge port; and said outer shell having a longitudinal dimension extending along an arcuate notional axis from the first end to the second end thereof;
    an elongated longitudinally arcuate tongue spaced apart from said outer shell and extending along a longitudinally arcuate interior surface of said outer shell, and said tongue having contoured peripheral edges adapted to only partially surround a length of the penis during use; and
    at least one spacer located intermediate the contoured peripheral edges of said tongue, and between said tongue and the interior surface of said outer shell.

12. A male incontinence device according to claim 11, and comprising a collection bag secured to the second end of said outer shell for receiving and collecting urine flowing outwardly through said discharge port.

13. A male incontinence device according to claim 11, wherein said tongue defines multiple perforations therein.

* * * * *